United States Patent [19]

von der Eltz et al.

[11] Patent Number: 4,615,981

[45] Date of Patent: Oct. 7, 1986

[54] PROCESS FOR OBTAINING CHOLESTEROL ESTERASE FROM MICROORGANISMS

[75] Inventors: Herbert von der Eltz, Weilheim; Helmgard Gauhl; Hans Seidel, both of Tutzing, all of Fed. Rep. of Germany

[73] Assignee: Boehringer Mannheim GmbH, Mannheim, Fed. Rep. of Germany

[21] Appl. No.: 663,149

[22] Filed: Oct. 22, 1984

[30] Foreign Application Priority Data

Nov. 11, 1983 [DE] Fed. Rep. of Germany ....... 3340950

[51] Int. Cl.⁴ .............................................. C12N 9/18
[52] U.S. Cl. ..................................... 435/197; 435/874
[58] Field of Search ................... 435/19, 23, 196, 197

[56] References Cited

U.S. PATENT DOCUMENTS

| | | | |
|---|---|---|---|
| 4,052,263 | 10/1977 | Masurekar et al. | 435/19 |
| 4,343,903 | 8/1982 | Beaucamp et al. | 435/197 |
| 4,360,596 | 11/1982 | Beaucamp et al. | 435/197 |

*Primary Examiner*—Blondel Hazel
*Attorney, Agent, or Firm*—Felfe & Lynch

[57] ABSTRACT

The present invention provides a process for obtaining cholesterol esterase from micro-organisms by culturing a micro-organism capable of forming cholesterol esterase in an appropriate nutrient medium in the presence of an inductor and obtaining the enzyme from the culture liquid and/or from the cells, therein the inductor used is a compound of the general formula:

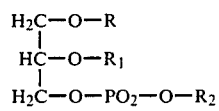

in which R and $R_1$ are alkyl or alkoxy radicals containing 14 to 18 carbon atoms and R or $R_1$ can also be a hydrogen atom and $R_2$ is an alkylamino radical containing 2 to 8 carbon atoms, an alkyl-trimethylammonium radical containing 3 to 8 carbon atoms, an alkylpyridine radical containing up to 4 carbon atoms in the alkyl moiety or a radical of the general formula $-CH_2-(CHOH)_n-CH_2OH$, in which n is a whole number of from 1 to 4.

11 Claims, No Drawings

PROCESS FOR OBTAINING CHOLESTEROL ESTERASE FROM MICROORGANISMS

The present invention is concerned with a process for obtaining cholesterol esterase from micro-organisms.

Cholesterol esterase has played an important part in clinical and biochemical analyses ever since processes for the enzymatic determination of cholesterol have been developed. Since a greater part of cholesterol in biological material is present in the form of esters, the joint use of cholesterol esterase and of cholesterol-oxidising enzymes, such as cholesterol oxidase or cholesterol dehydrogenase, also permits a completely enzymatic determination of cholesterol esters. This is known from Federal Republic of Germany Patent Specification No. 2,264,847. The cholesterol esterase from micro-organisms (see Federal Republic of Germany Patent Specification No. 2,506,712.3) has thereby proved to be especially useful in the scope of the determination of cholesterol.

As a rule, the previously found cholesterol esterase-producing micro-organisms require an inductor in order to form an amount of cholesterol esterase which makes working up worthwhile. By inductor there is to be understood a substance which stimulates the micro-organism to form the desired enzyme in larger amounts than without the use of an inductor, the inductor thereby being added to the nutrient medium used for the culturing.

Known inductors include fats and oils, such as olive oil, soya oil, sunflower oil, beef tallow, pork oil, groundnut oil, fatty acid esters, cholesterol esters and palmitic acid, as well as especially lecithin (see Federal Republic of Germany Patent Specification No. 2,933,646), with which hitherto the best results have been obtained with regard to the achievable amounts of enzyme.

However, a further increase of the enzyme yields would be desirable. Therefore, there is a need for making available still better inductors.

Surprisingly, we have found that the high proportion of unsaturated fatty acids in lecithin, as well as the choline group, are not optimal for the inductor action. Starting from this knowledge, the desired improvement can, therefore, be achieved, according to the present invention, using a new type of inductor.

Thus, according to the present invention, there is provided a process for obtaining cholesterol esterase from micro-organisms by culturing a micro-organism capable of forming cholesterol esterase in an appropriate medium in the presence of an inductor and obtaining the enzyme from the culture liquid and/or from the cells, wherein the inductor used is a compound of the general formula:

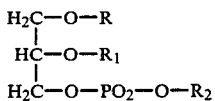

in which R and $R_1$ are alkyl or alkoxyl radicals containing 14 to 18 carbon atoms and R or $R_1$ can also be a hydrogen atom and $R_2$ is an alkylamino radical containing 2 to 8 carbon atoms, an alkyl-trimethylammonium radical containing 3 to 8 carbon atoms, an alkylpyridine radical containing up to 4 carbon atoms in the alkyl moiety or a radical of the general formula $-CH_2-(CHOH)_n-CH_2OH$, in which n is a whole number of from 1 to 4.

According to the present invention, it is possible to improve the yields of cholesterol esterase, referred to the same amount of inductor, by up to several 100% in comparison with lecithin. Within the scope of the present invention, the best results have thereby been obtained with compounds of the cephalin series ($R_2$=alkylamino) or of the phosphopolyol series ($R_2$=$-CH_2-(CHOH)_n-CH_2OH$) and of the phosphoalkylpyridine series.

Furthermore, we have found that amongst the saturated fatty acid residues, i.e. the alkoyl radicals, the stearoyl group displays a particularly good effectiveness, especially when it is the 2-position of the glycerol molecule ($R_1$). In the case of an otherwise identical structure of the molecule, we have also found that somewhat better results are achieved when R and $R_1$ are different in comparison with the case in which R and $R_1$ are the same. Furthermore, when $R_2$ is an alkylamino radical, it is preferably an ethylamino radical.

The Table 1 given in the following Examples gives, for a series of inductors which can be used according to the present invention, the enzyme activities which are achieved under the conditions described in the Example. For the purpose of comparison, the results obtained with the use of soya lecithin are also given. It can be seen that a substantially improved enzyme yield is achieved with the inductors to be used according to the present invention. Similar results have also been achieved with numerous other inductors to be used according to the present invention. Thus, for example, very good enzyme yields have been obtained with the use of 1,2-dipalmitoyl-glycero-3-phosphoethanolamine, 1,2-dipalmitoyl-glycero-3-phosphohexanolamine, 1,2-dimyristoyl-glycero-3-phosphoglycerol, 1,2-dimyristoyl-glycero-3-phosphoethanolamine and phosphopropanolamine, 1-palmitoyl-2-tetradecylglycero-3-phosphoethanolamine, 1-octadecyl-2-tetradecyl-glycero-3-phosphoethanolamine, 1-palmitoyl-2-stearoyl-glycero-3-phosphotrimethylammonium propanol and 1-hexadecyl-glycero-3-phosphoethanolamine.

The inductors used according to the present invention are preferably also used as a source of carbon and especially as the sole carbon source for culturing the micro-organisms. However, if desired, it is also possible to add separate sources of carbon, for example maize steep liquor. peptones, yeast extracts, sugar or polyalcohols.

The amount of inductor used in the case of the process according to the present invention corresponds to that of the known inductors. In general, it is from about 0.1 to 5% by weight, referred to the volume of the nutrient medium, the preferred amount being from 0.5 to 2% by weight.

As micro-organisms, within the scope of the process according to the present invention, there can be used all micro-organisms which are capable of forming cholesterol esterase in amounts making working up thereof worthwhile. Typical examples of appropriate micro-organisms are given in U.S. Pat. No. 4,343,903 to Beaucamp et al.

The other culturing conditions can also be taken over unchanged from those of the known processes, for example those mentioned above. In general, the most favourable culturing conditions for the particular micro-organism used are of importance, whereas the nature of the inductor used normally does not influence the culturing conditions.

The following Examples are given for the purpose of illustrating the present invention:

EXAMPLES 1 TO 7

For pre-culturing, 150 ml. of standard medium I of Merck were placed in a 500 ml. Erlenmeyer flask and inoculated with a loop full of material of the strain *Pseudomonas spec.* DSM 1280 and shaken for 15 hours at 28° C. The turbid solution obtained was diluted 1:20 with water. The tubidity measurement at 400 and 600 nm gave E=0.170. 100 ml. of the particular inductor-containing medium of the composition given hereinafter were inoculated with 1% of the above-described pre-culture and shaken at 28° C. in a 500 ml. Erlenmeyer flask. The inductor-containing medium contained, per litre of solution, the following substances:

7 g. disodium hydrogen phosphate heptahydrate
3 g. monopotassium dihydrogen phosphate
1.5 g. urea
0.6 g. magnesium sulphate heptahydrate
0.1 g. calcium chloride
0.1 ml. ferric chloride hexahydrate solution (1 g./100 ml.)
0.1 ml. zinc sulphate heptahydrate solution (1 g./100 ml.)
50 mg. sodium chloride
10 g. inductor.

The pH value of the medium was 7.0.

The clolesterol esterase activity was determined at different times in the culture, using cholesterol oleate at a temperature of 25° C. The following Table 1 shows the inductors employed and the activities in U/liter achieved after 3 days. For comparison, there was also used the most effective known inductor, namely lecithin.

TABLE 1

| example | inductor compound | U/liter |
|---|---|---|
| 1 | 1,2-dipalmitoyl-glycero-3-phospho-glycerol | 3500 |
| 2 | 1,2-dipalmitoyl-glycero-3-phospho-3-hydroxymethylpyridine ester | 5500 |
| 3 | 1,2-distearoyl-glycero-3-phospho-ethanolamine | 6500 |
| 4 | 1-palmitoyl-2-stearoyl-glycero-3-phosphoethanolamine | 9000 |
| 5 | 1-stearoyl-2-myristoyl-glycero-3-phosphoethanolamine | 5000 |
| 6 | 1-myristoyl-2-stearoyl-glycero-3-phosphoethanolamine | 7000 |
| 7 | soya lecithin (comparison) | 2500 |

Since all of the above-given values were obtained under the same conditions, they are exactly comparable.

We claim:

1. In a process for obtaining cholesterol esterase from micro-organisms by culturing a micro-organism capable of forming cholesterol esterase in an appropriate nutrient medium in the presence of an inductor and obtaining the enzyme from the culture liquid and/or from the cells, the improvement comprising said inductor being a compound of the formula:

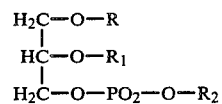

wherein R and $R_1$ are alkyl or alkoxy containing 14 to 18 carbon atoms or are hydrogen atoms; and
$R_2$ is alkylamino containing 2 to 8 carbon atoms, alkyl-trimethylammonium containing 3 to 8 carbon atoms in the alkyl moiety, alkylpyridine containing up to 4 carbon atoms in the alkyl moiety or a radical of the formula $-CH_2-(CHOH)_n-CH_2OH$, in which n is a whole number of from 1 to 4.

2. The process of claim 1, wherein $R_2$ is ethylamino.
3. The process of claim 1 wherein at least one of R and $R_1$ is stearoyl.
4. The process of claim 1 wherein R and $R_1$ are different.
5. The process of claim 4, wherein $R_1$ is stearoyl.
6. The process of claim 1 wherein $R_2$ is a glycerol residue.
7. The process of claim 1 wherein the inductor is used in an amount of from 0.1 to 5% by weight, referred to the volume of the nutrient medium.
8. The process of claim 7, wherein the inductor is used in an amount of from 0.5 to 2% by weight, referred to the volume of the nutrient medium.
9. The process of claim 2 wherein at least one of R and $R_1$ is stearoyl.
10. The process of claim 1 wherein $R_1$ is a stearoyl.
11. The process of claim 1 wherein said inductor is selected from the group consisting of
1,2-dipalmitoyl-glycero-3-phosphoethanolamine,
1,2-dipalmitoyl-glycero-3-phosphohexanolamine,
1,2-dimyristoyl-glycero-3-phosphoglycerol,
1,2-dimyristoyl-glycero-3-phosphoethanolamine,
1,2-dimyristoyl-glycero-3-phosphopropanolamine,
1-palmitoyl-2-tetradecyl-glycero-3-phosphoethanolamine,
1-octadecyl-2-tetradecyl-glycero-3-phosphoethanolamine,
1-palmitoyl-2-stearoyl-glycero-3-phosphotrimethylammonium propanol and 1-hexadecyl-glycero-3-phosphoethanolamine.

* * * * *